(12) United States Patent
Canyon et al.

(10) Patent No.: US 10,299,448 B2
(45) Date of Patent: May 28, 2019

(54) METHOD AND APPARATUS TO IMPROVE CROP YIELDS AND INCREASE IRRIGATION EFFICIENCY IN AGRICULTURE

(71) Applicants: James Canyon, San Diego, CA (US); Robert Bruce Ganton, San Diego, CA (US)

(72) Inventors: James Canyon, San Diego, CA (US); Robert Bruce Ganton, San Diego, CA (US)

( * ) Notice: Subject to any disclaimer, the term of this patent is extended or adjusted under 35 U.S.C. 154(b) by 487 days.

(21) Appl. No.: 14/308,514

(22) Filed: Jun. 18, 2014

(65) Prior Publication Data

US 2015/0366149 A1 Dec. 24, 2015
US 2017/0202159 A9 Jul. 20, 2017

Related U.S. Application Data

(60) Provisional application No. 61/844,840, filed on Jul. 10, 2013.

(51) Int. Cl.
*A01G 25/16* (2006.01)
*G01N 27/22* (2006.01)
*G05B 15/02* (2006.01)

(52) U.S. Cl.
CPC ......... *A01G 25/167* (2013.01); *G01N 27/223* (2013.01); *G05B 15/02* (2013.01); *Y02A 40/238* (2018.01)

(58) Field of Classification Search
CPC .... A01G 25/167; G05B 15/02; G01N 27/223; G01N 27/048; G01N 27/02; G01N 27/121; G01N 27/225; G01N 9/24; G01N 19/10; G01N 2223/1013; G01N 23/005; G01N 23/06; G01N 23/203; G01N 33/0032; G01N 15/06; G01N 15/0606
USPC .......................................... 700/284; 324/664
See application file for complete search history.

(56) References Cited

U.S. PATENT DOCUMENTS

| | | | | |
|---|---|---|---|---|
| 4,793,181 A | * | 12/1988 | Djorup | G01N 27/121 73/29.02 |
| 4,941,501 A | * | 7/1990 | Bireley | E02B 13/00 137/78.3 |
| 5,740,031 A | * | 4/1998 | Gagnon | A01G 25/167 700/16 |
| 7,135,871 B1 | * | 11/2006 | Pelletier | G01N 22/04 324/640 |
| 8,947,102 B1 | * | 2/2015 | Evett | G01N 27/223 324/600 |
| 2004/0083833 A1 | * | 5/2004 | Hitt | A01G 25/167 73/866 |

(Continued)

OTHER PUBLICATIONS

Ekmekci et al. (Appl Phys A (2013) 110:189-197).*

*Primary Examiner* — Ryan A Jarrett

(57) ABSTRACT

An irrigation control system is described for optimizing water used for growing crops. The irrigation control system uses a moisture sensor to measure soil moisture by measuring directly the relative phase velocities of different modes of propagation along a metallic structure mounted to a dielectric substrate. The average phase velocity is a function of the water content of the soil. The water content measurement is then transmitted to a central controller which then, through a set of heuristic algorithms, regulates the water distributed to the soil in a spatial and temporal manner.

20 Claims, 6 Drawing Sheets

(56) References Cited

U.S. PATENT DOCUMENTS

| | | | | |
|---|---|---|---|---|
| 2004/0145379 A1* | 7/2004 | Buss | .................... | G01N 27/223 |
| | | | | 324/664 |
| 2005/0087620 A1* | 4/2005 | Bowers | ................ | A01G 25/167 |
| | | | | 239/63 |
| 2009/0219037 A1* | 9/2009 | Campbell | ............ | G01N 33/246 |
| | | | | 324/664 |
| 2009/0302870 A1* | 12/2009 | Paterson | .............. | A01G 25/167 |
| | | | | 324/670 |
| 2013/0217332 A1* | 8/2013 | Altman | .................. | H04H 60/90 |
| | | | | 455/41.2 |
| 2013/0308675 A1* | 11/2013 | Sneed | .................... | G01N 25/00 |
| | | | | 374/121 |
| 2014/0046611 A1* | 2/2014 | Bloemendaal | ....... | G01N 27/223 |
| | | | | 702/65 |
| 2014/0113828 A1* | 4/2014 | Gilbert | ................. | H01L 39/126 |
| | | | | 505/100 |

\* cited by examiner

Cross Section of broadside Coupled lines on a substrate in air

For Dry Soil conditions 302

For Wet Soil conditions 303

Wired sensors

METHOD AND APPARATUS TO IMPROVE CROP YIELDS AND INCREASE IRRIGATION EFFICIENCY IN AGRICULTURE

RELATED APPLICATIONS

This application claims priority to U.S. provisional application No. 61/844,849, filed Jul. 10, 2013 and entitled "A method and apparatus to improve crop yields and minimize water usage in agriculture," which is incorporated herein in its entirety.

FIELD OF THE INVENTION

The present invention relates to a method and device that measures soil moisture and determines an advantageous and highly efficient irrigation scheduling. In one particular embodiment, the invention uses to simple sensor that measures moisture phase velocity, with the sensor communicating to one or more a centrally located controllers to set and adjust the watering of agricultural plants.

BACKGROUND

Most of the world is suffering in a chronic state lacking fresh drinking water. This leads to a shortage of water for agriculture, which makes it expensive or impossible to grow crops effectively. Increased need for water conservation in recent years has led to higher food prices and higher costs for farmers and consumers alike. The need for conservation has stemmed from higher demands on food production and higher population bases in localized areas. Water authorities around the United States, and the world are enacting watering limits and water usage expectations to ensure the valuable resource is being used carefully. In addition to agricultural needs, residential, sporting and landscaping all consume water at an alarming rate. It has been shown that in commercial crops, the amount of water used will greatly affect the profitability of the farm and therefore farmers are economically motivated to use the water carefully. Residential users of water are also motivated to conserve water for economic reasons.

It would be desirable therefore to have an innovative sensor technology such that an accurate watering regime can be constructed to optimize the use of this precious resource. By adding a wireless capability to the sensor, large areas can be monitored and optimized at extremely low costs, thereby improving the production of food and other agricultural products. Since it is clear that water conservation is important for society, this invention describes a method and apparatus to be able to enable optimal water usage for a given landscape or crop. Choosing crops with lower water requirements, or landscapes with lower water requirements are alternative methods to reduce water usage. The subject of this invention is to, for a given crop or landscape, enable the water user to reduce the water usage to the optimal point and therefore minimize the cost of water, or optimize the yield in the growing of commercial food crops.

In order to enable this ability several pieces of technology are necessary. Some of the technology has been developed and some of the technology is the subject of this invention. In order to optimize cost further, technology choices were made to enable the optimal cost structure. Other choices could yield similar results in terms of water usage and therefore could still result in significant savings for the user, however they would not yield the ideal cost savings.

SUMMARY OF THE INVENTION

An irrigation control system is described for optimizing water used for growing crops. The irrigation control system uses a moisture sensor to measure soil moisture by measuring directly the relative phase velocities of different modes of propagation along a metallic structure mounted to a dielectric substrate. The average phase velocity is a function of the water content of the soil. The water content measurement is then transmitted to a central controller which then, through a set of heuristic algorithms, regulates the water distributed to the soil in a spatial and temporal manner.

An important advantage of using this technique is that moisture measurements are made with no electrical contact to the soil and therefore no chance of conduction by or corrosion of the system, thereby yielding a more accurate and longer trouble free operation cycle compared to existing solutions in the market. This method and apparatus allows cost effective water conservation while maintaining optimal growing conditions.

DETAILED DESCRIPTION OF THE PREFERRED EMBODIMENT

Generally, the present invention is directed to a cost effective mechanism and process that is enabled to automatically control the application of water to crops or landscapes in a highly efficient manner. The devices and processes disclosed herein may be used for providing efficient irrigation for plants in both the commercial and residential markets. That is, the devices and methods are easily provided to manage irrigation of a home garden and landscape, but are readily to scale to manage large commercial agricultural undertakings such as farming, grazing, and foresting.

Figure 1:
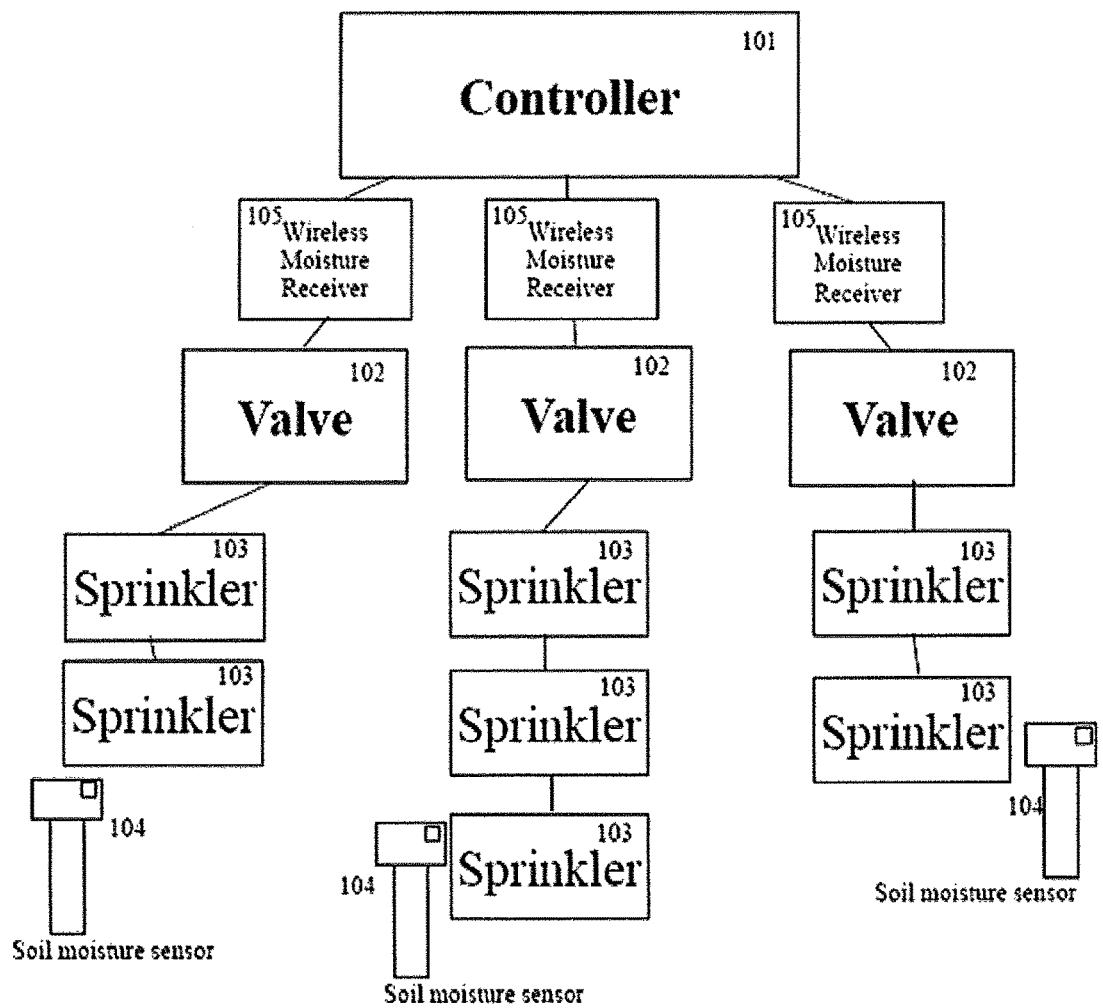
FIG. 1 is a simplified block diagram of an irrigation control system in accordance with the present invention.

Referring to FIG. 1, one embodiment of the invention is illustrated. As shown, a central controller 101 is used to manage several zones of irrigation, with each zone having a valve 102 and a set of associated sprinklers 103, drippers, drip lines, or other irrigation delivery apparatus. Although three zones are illustrated, it will be appreciated that fewer or more zones may be used. Generally, the controller 101 is used to determine at what time each valve 102 is opened to deliver water to a particular zone, and how long each valve 102 is left open, which can be different for each zone. The controller can also define a rate of delivery for the water, which may be different for each zone. Often, multiple valves are controlled in a round-robin manner, with only one valve opened at a time. Further, the controller generally has a local or network input for accepting irrigation information. For example, the controller may allow a farmer to set the expected time for each value is to be open, as well as a weekly schedule for when each watering cycle is to begin. It will be appreciated that there are many known ways that an irrigation controller can be instructed as to the desired level of irrigation to be applied over a period of time.

A wireless moisture receiver 105 is operably coupled between the controller 101 and the Valve 102. The wireless moisture receiver 105 can be physically integrated into the valve or controller, or may be a separate device Further, here although there is a one to one relationship between the wireless moisture receivers 105 and the valves 102, it will be understood that the number of valves does not necessarily have to equal the number of wireless moisture receivers 105. Each wireless moisture receiver 105 is constructed to receive moisture information from one or more soil moisture sensors 104. In the simple embodiment shown in FIG. 1, each wireless moisture receiver 105 can use the measurements from its associated soil moisture sensor 104 from its zone to modulate the length of time the valve 102 is actually open and therefore curtail watering when moisture objectives are met. In this way, the actual moisture content of the soil is measured, and in near real time that information is used to shorten or lengthen irrigation time to meet the desired level of water application. In this way, the plants are assured the correct and advantageous amount of moisture, and the amount of water used is kept at the minimum amount. Accordingly, water is delivered to the plants in a highly efficient and conservation-aware manner. This is in contrast prior known control devices where controller has limited information to determine when the watering has been completed other than a timing circuit, which leads to the waste of water due to over-watering, or reduced plant health due to under watering.

Additionally, the system of FIG. 1 can use the length of time the controller 101 is attempting to water as a gauge as to whether the user want a generally damper soil or generally drier soil. By determining whether the length of time the controller 101 is increasing from watering cycle to watering cycle can allow the heuristic algorithm in the wireless moisture receiver 105 to adjust its moisture target accordingly. A user can increase the watering time allotted to a valve if it is perceived that the system is not applying enough water for the plants or conditions in order to signal to the wireless moisture receiver 105 that the moisture target needs to be increased. In another embodiment, the controller 101 can have the wireless moisture receiver 105 embedded within it. This would have the advantage of a slightly less expensive solution with the added requirement that the radio coverage be adequate over a greater area. In addition, the installation and provisioning of such a system would be slightly more complicated than that the previously described embodiment.

The wireless moisture receiver 105 comprises a wireless radio transceiver that is coupled to a controller to make use of the received moisture data content. In one example, the moisture receiver 105 could be directly coupled to a switching circuit which allows the current to a solenoid valve operating an irrigation system to be controlled. The switching circuit may make use of a processor to make decisions as to when to open and close an irrigation valve. In an additional embodiment, the receiver could be connected to a network whereby it could deliver the moisture level to an operator, farmer, or larger computer system tasked with optimizing the use of water in the irrigation task.

The moisture sensor 104 comprises a transceiver which is coupled to an additional circuit which allows the accurate measurement of the frequency of an oscillator which varies based on moisture content of the soil, as explained in more detail in a following section. In the simplest case, the moisture sensor can send its moisture information periodically in wireless advertising packets whereby it would expect no acknowledgement and would have no way to determine if the data was being received. In another embodiment, the sensor could advertise that it has a new moisture measurement to transmit and the moisture receiver could then initiate a connection to collect said reading. In some cases, the moisture receiver could be a moisture sensor acting as a multihop node to conduct the measurement to the root of the network (hop 0 node).

Although FIG. 1 shows that a single moisture receiver is associated with a single moisture sensor, it will be appreciated that multiple moisture sensors can be used to provide a more complete assessment of watering needs throughout a zone. For example, moisture sensors may be distributed in various areas within a zone to assess moisture in several places. In another example, the moisture sensors may be spaced apart vertically at one location to assess the moisture content at various depths of the soil.

The simplest algorithm for a low cost sensor/controller pair allows the watering scheme to operate from the irrigation controller in a manner similar to the mode prior to the moisture sensor capability being added. The moisture sensor 104 measures the water content of the soil and sends data indicative of the soil's moisture content to the moisture receiver 105. The data may be in a final form that indicates a specific water content, or may be in the form of a measurement or other data that requires further processing at the receiver 105 to determine the actual water content. The moisture receiver 105 applies a moisture comparison process to decide whether to water more or less based on previous moisture levels. The goal is to always drive the moisture content toward a specific target. The moisture receiver 104 collects the moisture level and either turns the sprinkler valve off earlier or later than the previous watering cycle based on whether the moisture is higher or lower than before. In this way, the moisture sensor/system can always be targeting an optimal level of moisture despite changes in environment or watering cycles. Additionally, the sensor system can Else a more advanced algorithm which accepts multiple moisture readings through a watering cycle and determines levels of field capacity and approximate wilt response. Using this information, the watering cycle can be fully adjusted. In some cases, watering can be completely deferred due to adequate moisture. In severe drought conditions, additional watering cycles can be added to ensure crop success.

Figure 2:
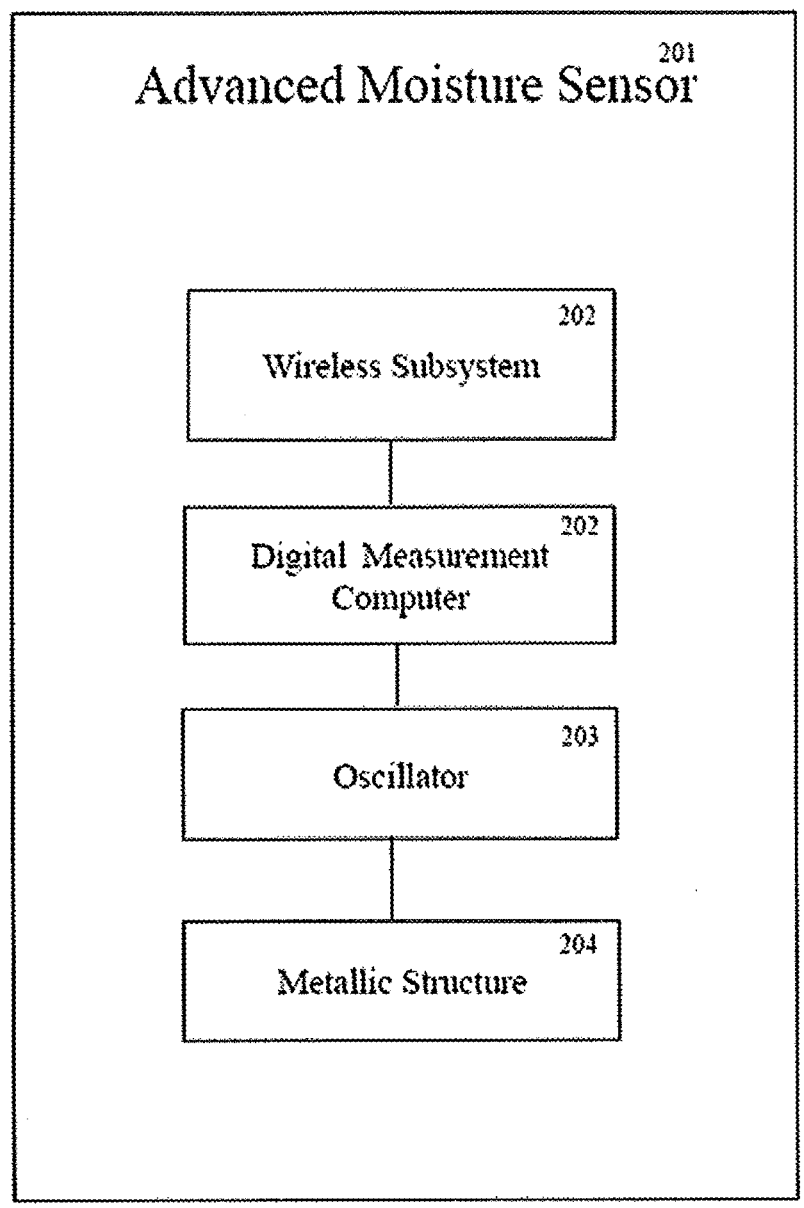
FIG. 2 is a simplified block diagram of a moisture sensor for use in an irrigation control system in accordance with the present invention.
Figure 3:
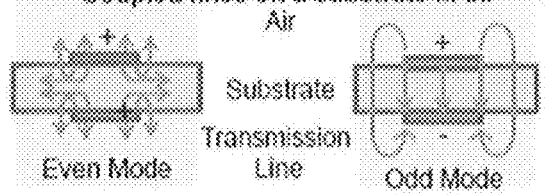
FIG. 3 is an illustration of a moisture sensor for use in an irrigation control system in accordance with the present invention.
Figure 3:
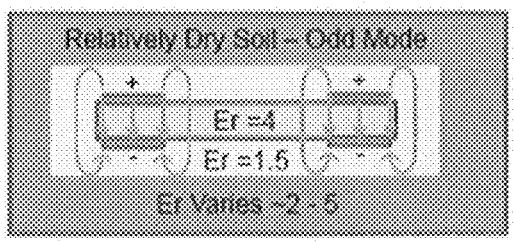
Figure 3:
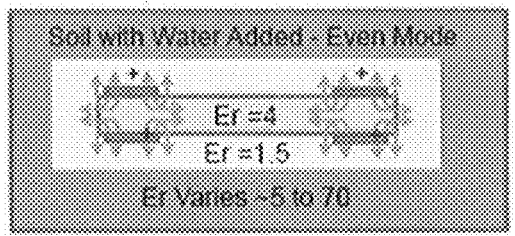

The water moisture sensor 105 is further described with reference to FIG. 2. There are many types of moisture sensors. Moisture content of soil may cause variations to direct measurements on a soil probe for resistance, capacitance, temperature, but these have been used with varying degrees of success, and tend to use probes that are subject to degradation over time. In contrast, moisture sensor 201 only indirectly measures water content by measuring 202, 203 the average phase velocity of the electromagnetic waves in a metallic structure 204 when the sensor is embedded in the soil. Different types of soil have similar dielectric constants, but water has a much higher relative dielectric constant, which enable accurate indirect moisture content measurement for a wide range of soil types. As shown in FIG. 3, we use a radio frequency structure (301, 302, 303) to effectively radiate electromagnetic fields/waves into the soil. As a result, we are able to average moisture content over a much larger volume of soil than conventional sensors. By being able to do this, we can yield results which have much higher accuracy. Conventional sensors can have problems by being inserted near rocks, roots, or in areas where small air pockets exits. All these possibilities can lead to measurement errors and incorrect moisture assessments. The details of this are included in the theory of operation which follows.

Finally, in order to make this a viable technology, a very low cost, very low power wireless link 202 is necessary for deployment. Bluetooth technology has further developed an even lower power technology called Bluetooth Smart or Bluetooth Low Energy. The widespread adoption of this technology and careful design, have made it the perfect solution for our wireless deployment model. Of course other low power wireless standards are available and if used would yield great water savings, in order to deliver this solution to the greatest effect, it is necessary to have the absolute lowest price point. Bluetooth Low Energy solutions are the lowest cost method of delivering this data. The one area where Bluetooth Low Energy (BLE) has difficulty is in its ability to form networks. Bluetooth Classic (BT 1.1, 2.0, 2.1, 3.0) all have the ability to form small networks called piconets.

The disclosed embodiment includes a mechanism to allow BLE to form similar mesh networking structures to enable multihop delivery of data to extend the reach of the wireless solution. Multihop is implemented utilizing device discovery, time synchronization, and communication protocol.

Device Discovery and Time Synchronization

It is important to note the disclosed system has the ability to operate with no on or off switch or user control. Devices are turned on by inserting them into water for a period of time on the order of 15 minutes. Once the sensor is placed in water the sensor starts its advertising mode. During advertising/inquiry, the sensor advertises and receives advertisements from other sensors and controllers thereby cataloguing the names of devices in the network including the controller. Once the sensor receives communication with the controller, all sensors in the group synchronize their time with the controller and initiate hopping intervals we call A, B and C where A and B are advertising and receiving intervals and C is a dormant interval. This seemingly simple task solves group identification and timing issues in a very efficient manner. It is true that other wireless technologies or strategies could be employed to deliver the same water savings, it is important to note that using the lowest cost method will allow the broadest adoption of our technology and thus have the greatest benefit for the world and its water sources.

Communication Protocol

Figure 4:
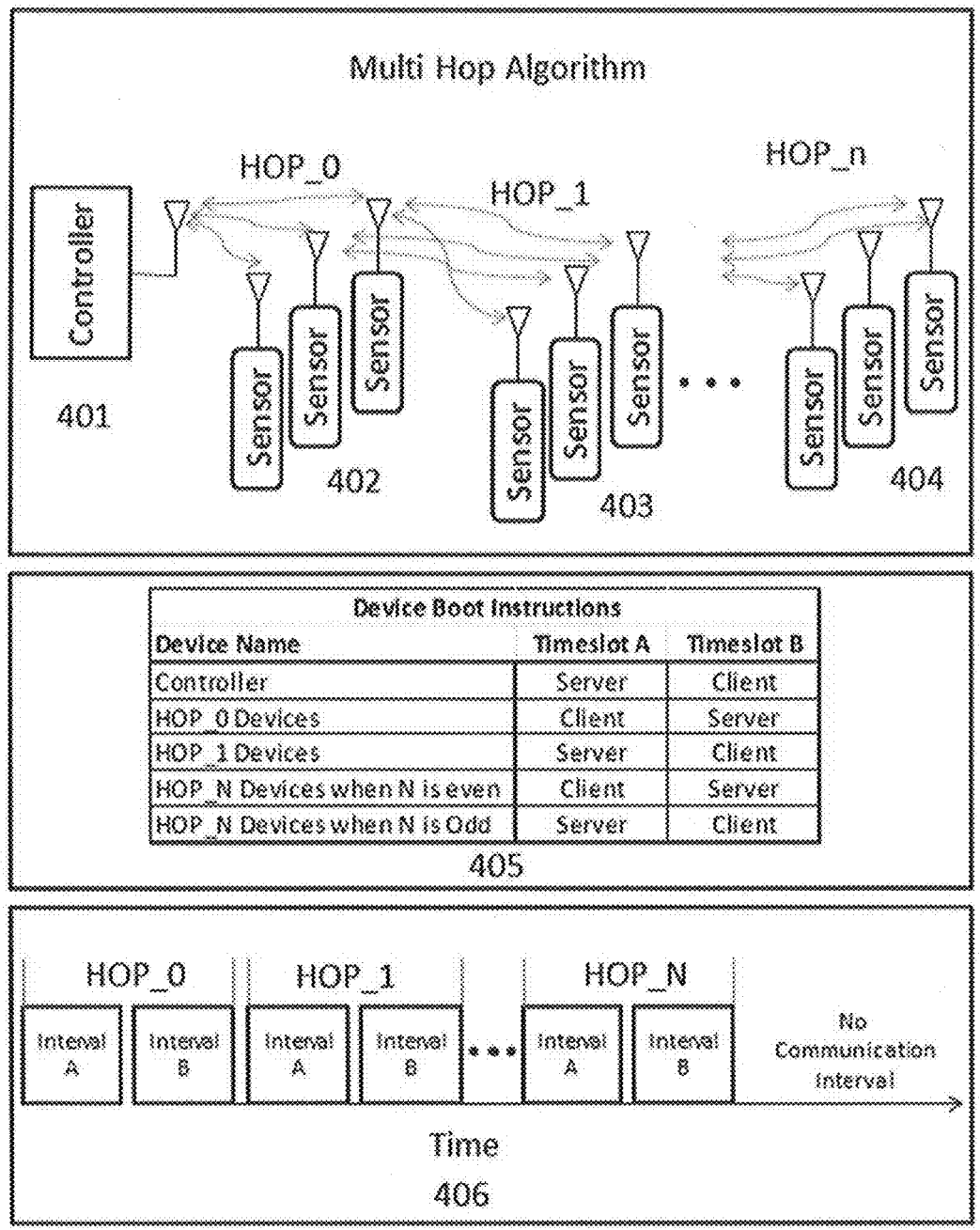
FIG. 4 is an illustration for a communication protocol for use in a moisture sensor in an irrigation control system in accordance with the present invention.

FIG. 4 depicts communication between devices is managed by setting up two communication intervals, we will call interval A and interval B. FIGS. 405 and 406 show the controller becomes server and receives in interval A and becomes client and transmits in interval B. FIG. 401-404 show a system of multiple sensors installed mimicking a real life scenario. Initially all sensors are labeled as HOP_0 sensors and therefore become clients and transmit in interval A and become servers and receive in interval B. Sensor group 402 can talk directly to the controller thereby earning the right to be HOP_0 sensors and the remaining sensor groups 403 and 404 are not in range of the controller. After a period of no communication with the central controller, sensors switch identify to become HOP_1 sensors and attempt communication with HOP_0 sensors and HOP_3 sensors. Sensors alternate between Timeslot A and B intervals looking for HOP_N−1 and HOP_N+1 sensors to communicate with until a link is established as depicted in FIGS. 404-406. The algorithm is robust due to the fact that there are only 2 time slots to transmit in and only 2 time slots to receive in. The algorithm is also efficient due to the fact that data flows in two directions from the master to the slaves and from the slaves to the master simultaneously. Data from the furthest slave will reach the master after n hops and vice versa. Timing requirements are much relaxed from bluetooth low energy connected specifications. Absolute timing between devices is communicated by transmitting absolute time as defined by the controller in the form of a time stamp during each communication session to each slave noting absolute time is the transmitted time plus number of hops times the transmit receive time.

Theory of Operation

The moisture sensor 201 has several important and unique aspects. Broadly, the sensor is a metallic structure 204 separated by a dielectric and encased by a dielectric which is immersed in the soil to be measured. This structure can be hermetically sealed to that it has no conductive path to the soil whatsoever. Performance is optimal if this is the case. This structure is designed to project electric fields into the soil as shown with reference to FIG. 3. Second there is an oscillator 203 which is using the effective electrical length of the metallic structure 204 to provide a feedback loop to use for a frequency determining element for the oscillator 203. The oscillator 203 will oscillate at the frequency determined by the electrical length of the metallic structure 204. Often, the metallic structure 204 will take the form of multiple transmission lines, as shown in FIG. 3. The electrical length of the metallic structure 204 is dependent on its physical size, which is fixed for a given sensor, and the phase velocities of the signal traveling along the sensor transmission line. Third is the location of the transmission line in as it corresponds to another transmission line in proximity.

The disclosed moisture sensor deploy multiple transmission lines such that two or more transmission lines electrically couple to each other. Coupled lines exhibit an even mode impedance and an odd mode impedance. The impedance and phase velocities of even and odd modes of propagation are dependent on the geometry of the conductors and dielectric constants of the volumes surrounding the coupled lines. The impedance and phase velocity along coupled lines is defined by the average of the even mode and odd mode impedances and the phase velocities along coupled lines is defined by the average of the even mode and odd mode phase velocities also. The average velocity is the metric measured by the sensor. Careful placement of the coupled lines in relationship to each other and a substrate of known dielectric constant and a dielectric (like soil) of an unknown dielectric constant can be optimized such that one mode of propagation favors measurement of the known dielectric constant and one mode favors the measurement of the unknown dielectric constant.

Figure 5:
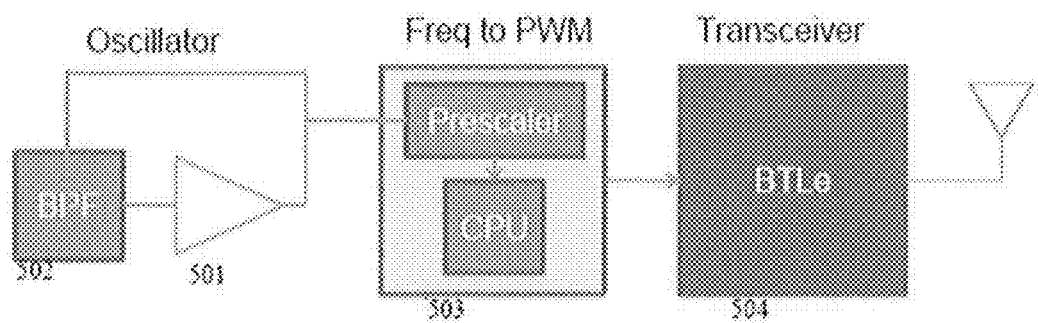
FIG. 5 is an illustration of electronic circuitry arranged in a moisture sensor for use in an irrigation control system in accordance with the present invention.

The simplest example of this is the placement of two transmission lines on opposition sides of a known dielectric with the unknown dielectric surrounding the substrate as illustrated in FIG. 3. In this case the odd mode impedance and phase velocity are primarily determined by the geometry of the known dielectric, in this example the substrate. The even mode impedance and phase velocity are primarily determined by the unknown dielectric constant, thus creating a method to measure an unknown dielectric constant. Fourth there is a high frequency pre-scaler embedded within a microprocessor 503 as illustrated in FIG. 5. FIGS. 501, 502, 503, and 504 describe in block diagram form an example of a single moisture sensor measurement system consisting of an oscillator 501+502, a Frequency to Pulse width modulator (PWM) 503 and a transceiver 504. FIGS. 501 and 502 depict an oscillator comprised of our soil moisture sensor 502 which through the use of matching elements and simple filter design techniques provides a bandpass frequency (BPF) response which limits the range of oscillation of the resultant oscillator. The oscillator is fed to a prescaler 503 which is deployed as a low cost method to translate a high frequency input into a lower frequency output by dividing the high frequency by a programmable number such that the output pulse width is much lower than the reference oscillator which runs the CPU. This allows the CPU located in 503 or 504 the ability to measure the pulse width as a multiple of very accurate clock counts. The result of this comparison produces a measurement which is related to the water content of the soil. Once the microprocessor 503 or 504 has calculated the water content, it will transmit this value to the controller via wire or wireless communication sub-system 504 which will enable the data to be delivered wirelessly to a centralized data collection facility. This facility will then compare readings and make watering decisions based on algorithms which have been heuristically determined optimal watering strategies. Optimal watering strategies pay attention to key soil moisture levels, soil saturation (maximum amount of water soil can hold), field capacity (amount of water the soil can hold after excess drainage has occurred), and wilting point (minimum amount of water in soil required for a plant not to wilt). Watering algorithms attempt to control over watering in two areas, by restricting each water event such that the soil reaches field capacity yet does not become saturated and by not watering until the soil comes close to the wilting point. Optimization of watering employs averaging previous measurements for field capacity optimization and water start times for wilting point optimization. Further inputs from real time weather including temperature humidity time of year, zip code and internet based weather forecast or collective water content measuring information which may be available on the internet can also be deployed to optimize watering profiles. One can appreciate that this optimization is ideal for commercial growing operations and may not be optimal in residential environments. In this case, alternative heuristics may be employed to provide schemes more appropriate for residential environments where constraints are not as in the case of commercial growing operations.

The metallic lines mounted to a dielectric substrate can be formed in many different configurations. In all cases, they will present an effective lumped element circuit element of some combination to the circuit that follows. In traditional circuitry, transmission lines are referenced to a ground. In our case, we have selected broadside coupled lines this structure eliminates the need for a ground plane due to the self coupling and delivers a good compromise between soil penetration and electrical performance. The structure has been designed to deliver electromagnetic waves/fields into the soil such that the dielectric constant of the soil is the dominant factor in setting the phase velocity of the circuit element made up of the metallic lines which are mounted to a dielectric substrate.

The system works based on electromagnetic wave propagation on the metallic coupled lines. In any metallic conductor, the propagation speed (phase velocity) of the wave is related to the speed of light and the effective dielectric constant in the medium surrounding the metallic conductor. If the metallic conductor is in a vacuum, the speed (phase velocity) is roughly 186,000 miles per second, or $2.99 \times 10^8$ m/s. If the same wire is in air, the speed is slightly reduced because the dielectric constant of air is slightly greater than 1. Phase velocity in a particular structure is dependent on many factors, dimensions of the conductor, distance and dielectric constant in the vicinity of the conductor, and distance to a return path or ground. In the disclosed system, the metallic structure is designed to include a strong even mode and odd mode phase velocity mis-match so that it can optimize the ability to measure effective dielectric constant variations in the surrounding soil and do this without having to print a ground plane from which the transmission line impedance is referenced to. The phase velocity mis-match allows it to determine moisture content as a result.

Water has a very high dielectric constant relative to anything typically found in soil. This means that the water dielectric constant effect on the phase velocity is dominant beyond the soil variation. Using a heuristic algorithm, the variation due to soil variation can be subtracted out and ultimate water moisture content can be deduced. The dielectric constant allows electromagnetic wave and their associated electric fields to be concentrated in areas of higher relative dielectric constant. Air having a relative dielectric constant of nearly 1 does not concentrate the electric fields associated with electromagnetic waves. When materials of higher relative dielectric constant are in the presence of electric fields, the field will tend to concentrate in material with high relative dielectric constant. This concentration of the field within the different materials is one of the basis for why our invention works. When the electric fields concentrate in the higher relative dielectric materials, the propagation of the wave is impeded and therefore slows. This slowing of the propagation from nearly the speed of light to less than the speed of light allows us to measure the effective relative dielectric constant of the material surrounding our sensor.

Because it is known very accurately what the sensor relative dielectric constant is, and what the dielectric constant of water is, and the range of dielectric constants are known for various soil types, the system can accurately predict the percentage of water within the soil mixture surrounding the sensor. There are two very important consequences of the previous statement: 1) The system is effectively able to integrate the water concentration in a relative large volume to make decisions about water content; and 2) as the relative dielectric constant of water is much higher than both the sensor and the soil, the water content dominates the effect we are measuring and it is therefore possible to make accurate predictions. In order to determine the speed of the electromagnetic wave propagation in the vicinity of the sensor, we have developed a low cost oscillator. The speed is measured by measuring the time it takes for one cycle of electromagnetic wave to propagate around our structure. Changing the size and complexity of the structure will allow the frequency to get lower if the structure size is increased and the inverse is also true. The structures geometry will determine both the electrical and physical length, but will also determine the type of electromagnetic waves that propagate in the structure. This will in turn have an effect on the depth to which the waves penetrate the soil and water mixture. It is the joint optimization of the structure which allows accurate measurements of water content over relatively large volumes of water. This is important as small defects like air pockets, roots, or rocks can adversely affect the sensors who do not integrate their measurement over a relatively large volume.

The preferred oscillator is based on a dual gate FET. The amplifier can be configured in many configurations, although we have chosen a cascode configuration for optimal electrical performance at the frequencies used. We have chosen the frequencies to be providing a relatively large volume of soil to be measured while keeping power consumption of the device to a minimum. In our embodiment, the amplifier is configured with feedback from the metallic structure of broadside coupled lines to form an oscillator. The broadside coupled structure is matched to the amplifier using standard filter techniques, in this case a second order Tchebychev frequency response is used. Our impedance matching is designed to both optimize power consumption and phase variation as a function of the measurement range of even and odd mode impedances due to the sensor influence of air/soil/water of the resultant filter. This oscillator operates at between 10 MHz and 100 MHz. While these numbers are not necessarily ideal, they represent a good tradeoff between accuracy and low power operation.

The microprocessor was chosen for three characteristics primarily, low power operation, pre-scaler coupled to an internal counter, and finally a second free running counter with enough capacity to measure the frequency with the accuracy and speed with which we need to measure soil moisture. The following diagram outlines the internal signal arrangement specific to our embodiment. It is possible to use other alternatives to achieve the same effect, the ability to measure the frequency of our oscillator.

Figure 6:
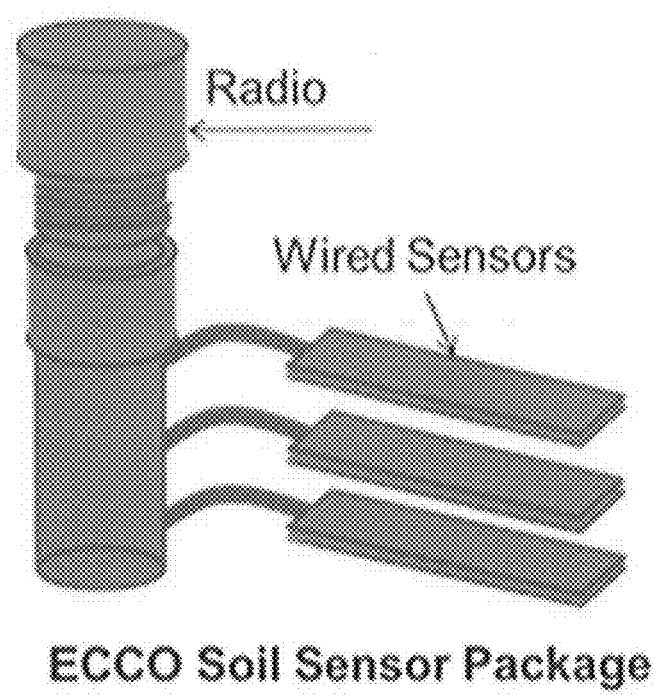
FIG. 6 is an illustration of an embodiment of a moisture sensor for use in an irrigation control system in accordance with the present invention.
Figure 7:
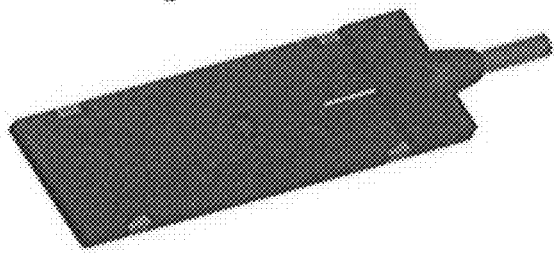
FIG. 7 is an illustration of an embodiment of a moisture sensor for use in an irrigation control system in accordance with the present invention.
Figure 8:
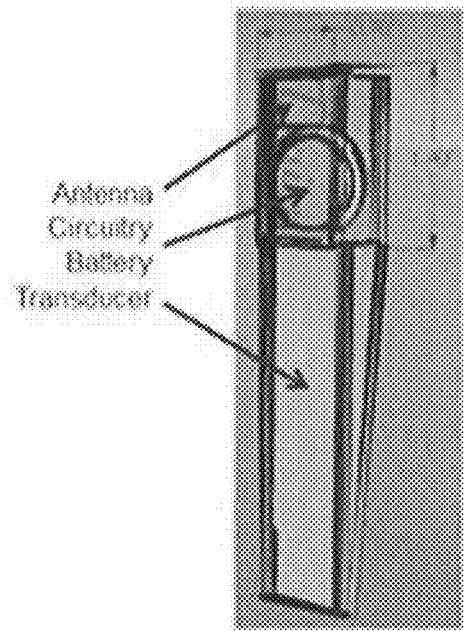
FIG. 8 is an illustration of an embodiment of a moisture sensor for use in an irrigation control system in accordance with the present invention.
Figure 9:
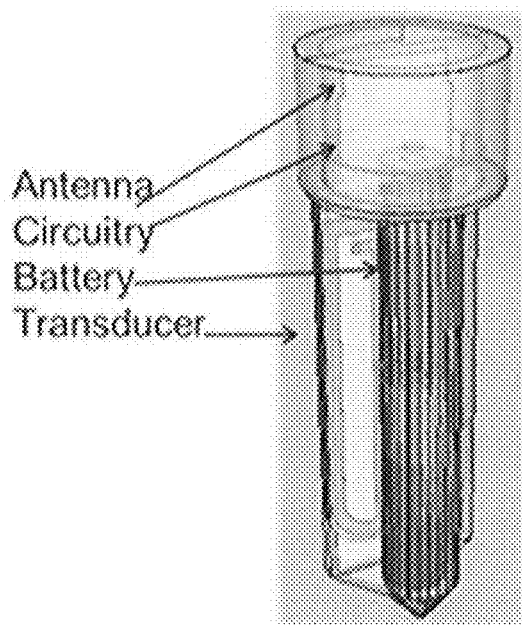
FIG. 9 is an illustration of an embodiment of a moisture sensor for use in an irrigation control system in accordance with the present invention.

Referring now to FIG. 6, an embodiment of a moisture sensor is illustrated. In this example, multiple sensors are positioned vertically in the soil to enable moisture readings to be taken at various soil depths. Data indicative of each moisture measurement may be communicated to a central receiver using the integral radio, or in some cases, local computing processes in the sensor body may average or otherwise evaluate the multiple (in this case 3) moisture readings and send processed data to the central receiver. FIG. 7 shows the detail of one moisture sensor described in FIG. 6. This sensor is comprised of components from FIG. 5 including the oscillator 501+502 and the prescaler+cpu as depicted in 503. This sensor is receives information from a controller in this case, the radio processor in FIG. 6 to program it to measure and report data including soil moisture, temperature and other parameters to be determined as designed to optimize crop yield. FIG. 8 and FIG. 9 show additional embodiments of the design as described in FIG. 5. Both of these devices contain the key elements of a moisture sensor described in FIG. 5, an oscillator 501+502, a frequency to pulse width modulator 503 and a transceiver 504. These physical embodiments differ from each other due to the application, the smaller device FIG. 8 is designed specifically for potted plants and contain with a smaller battery while the larger device in FIG. 8 is designed for outdoor turf measurements and contains a larger sensor surface yielding improved accuracy and a larger battery for improved sensor life. It will be appreciated that the moisture sensor can take many forms consistent with this disclosure.

While particular preferred and alternative embodiments of the present intention have been disclosed, it will be appreciated that many various modifications and extensions of the above described technology may be implemented using the teaching of this invention. All such modifications and extensions are intended to be included within the true spirit and scope of the appended claims.

What is claimed is:

1. A soil moisture sensor, comprising:
 a dielectric substrate;
 an embedded coupled metallic line structure mounted to the dielectric substrate and constructed to be driven in an odd impedance mode and an even impedance mode;
 a power source;
 radio frequency driving circuitry connected to the metallic line structure for radiating electromagnetic waves into the soil that drives the metallic line structure to generate an oscillation that has an odd mode phase velocity component and an even mode phase velocity component;
 a determination circuit that is configured with a frequency counter to determine an average phase velocity of the even and odd mode phase velocities by measuring the oscillation frequency along the metallic line structure; and
 wherein the average phase velocity of the even phase velocity and the odd phase velocity is a function of the water content in the soil.

2. The moisture sensor of claim 1 wherein the metallic line structure comprises a plurality of broadside coupled transmission lines.

3. The moisture sensor of claim 1 further comprising an oscillator and a high frequency counter, wherein the oscillation frequency is measured using the oscillator and the high frequency counter.

4. The moisture sensor of claim 3 wherein the high frequency counter comprises a low power low frequency oscillator and a pre-scaler circuit to extend the range of the frequencies that can be measured by the low power low frequency oscillator.

5. The moisture sensor of claim 1, further comprising a wireless communication circuit for sending data indicative of the water content to a receiver.

6. The moisture sensor of claim 5, wherein the wireless communication circuit is constructed to implement a Bluetooth compliant communication transmitter.

7. The moisture sensor of claim 6, wherein the data indicative of the water content of the soil is transmitted in an advertising payload section of a Bluetooth Low Energy packet.

8. The moisture sensor of claim 1 further comprising a radio frequency circuit to measure a dielectric constant of the soil by measuring the ratio of even mode and odd mode phase velocities, and wherein the metallic line structure is embedded in the substrate.

9. The moisture sensor of claim 8 wherein the metallic line structure comprises a plurality of structures at different lengths, and switching elements coupled to the structures that are constructed to enable water content measurements at multiple frequencies to improve overall measurement accuracy.

10. The moisture sensor of claim 8 wherein the metallic line structure is a microstripline structure.

11. The moisture sensor of claim 8 wherein the metallic line structure is a set of broadside coupled lines that have phase velocity variation based on the water content of the soil.

12. The moisture sensor of claim 1 wherein the determination circuity comprises a processor that is programmed to compare a frequency of oscillation to the rate of oscillation in free space to determine the water content in the soil.

13. The moisture sensor of claim 1 wherein the metallic line structure forms a low pass filter.

14. The moisture sensor of claim 1 wherein the metallic line structure forms a high pass filter.

15. The moisture sensor of claim 1 wherein the metallic line structure forms a transmission line.

16. An irrigation control system, comprising:
  a moisture sensor, further comprising:
    a dielectric substrate;
    an embedded coupled metallic line structure mounted to the dielectric substrate and constructed to be driven in an odd impedance mode and an even impedance mode;
    a power source;
    radio frequency driving circuitry connected to the metallic line structure for radiating electromagnetic waves into the soil that drives the metallic line structure to generate an oscillation that has an odd mode phase velocity component and an even mode phase velocity component;
    a determination circuit that is configured as a frequency counter to determine an average phase velocity of the even and odd mode phase velocities by measuring the oscillation frequency along the metallic line structure;
  a transmitter;
  a receiver; and
  a valve controller coupled to the receiver.

17. The irrigation control system of claim 16, wherein the valve controller executes algorithms to optimize the use of water for the purpose of enabling optimized growth of crops or other plants.

18. The irrigation control system of claim 17, wherein the algorithms are heuristic in nature.

19. The irrigation control system of claim 18, wherein the valve controller is constructed to receive temperature and light history information and to use this information in the heuristic algorithm as a prediction from current water cycle to next water cycle to implement a watering program including duration and/or start time.

20. The irrigation control system of claim 16 further including a wide-area network radio constructed to receive environmental data comprising insolation, precipitation, temperature or humidity, and the processor uses moisture content data from the sensor and environment data to adjust watering times and durations.

* * * * *